United States Patent [19]

van der Jagt

[11] Patent Number: Plant 5,870

[45] Date of Patent: Feb. 3, 1987

[54] CHRYSANTHEMUM 'WHITE REFLA'

[75] Inventor: Martinus van der Jagt, Ter-Aar, Netherlands

[73] Assignee: Chrysanthemum Breeders Association N.V., Willemstad & Curacao, Netherlands Antilles

[21] Appl. No.: 664,834

[22] Filed: Oct. 25, 1984

[30] Foreign Application Priority Data

Nov. 3, 1985 [NL] Netherlands ..... CHR 834

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Parkhurst & Oliff

[57] ABSTRACT

A new and distinct cultivar of Chrysanthemum plant named 'White Refla' bearing large sized white blooms with a green yellow center and having a performance of seventeen days.

3 Drawing Figures

BACKGROUND OF THE NEW PLANT

The new plant of the present invention relates to the Chrysanthemum genus.

ORIGIN AND HISTORY OF THE NEW PLANT

The new plant according to the present invention comprises a new and distinct cultivar of Chrysanthemum plant which is a color-mutant of Chrysanthemum named 'Pink Refla'. The new cultivar was discovered by Martinus van der Jagt in July, 1983 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a large sized bloom and white color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of chrysanthemum is of the botanical classification *Chrysanthemum morifolium,* named 'White Refla'. When grown in the vicinity of Ter Aar, Holland, it has a response time of approximately eight and one-half weeks. This new variety produces large sized white blooms with a green yellow center having a performance of seventeen days. This new variety Chrysanthemum has been found to retain its distinctive characteristics throughout successive propagations and may be planted under conventional greenhouse conditions in Holland between weeks 01–34.

The following is a description of the plant and characteristics that distinguish it over related known varieties and its antecedents:

Botanical classification: *Chrysanthemum morifolium.*

Bud:

- *Size.*—Medium (Cross-section 1.5 cm.; length 1 cm. approx.).
- *Form.*—Flat top.
- *Color.*—Lemon Yellow R H S 4/3.

Bloom:

- *Size.*—Large.
- *Fully expanded.*—7–8.5 cm. (approx.).
- *Borne.*—Single.
- *Stems.*—Strong.
- *Forms.*—Single.
- *Permanence.*—17 days.

Color:

- *Center of flower (Disc Floret).*—Willow Green R H S 000862+Yellow Ochre R H S 07.
- *Base of petals.*—White with tint Empire Yellow R H S 603/2.
- *Inside of petals.*—Pure White.
- *Reverse of petals.*—Pure White.
- *Outer petals.*—Pure White.
- *Tonality from a distance.*—Large attractive white flower with upstanding petals.
- *Discoloration.*—White from the beginning to maturity.

Petals:

- *Texture (upper and underside).*—Rough.
- *Rows.*—3.
- *Number.*—35–43.
- *Arrangements.*—Imbricated.
- *Persistence.*—Petals strong. Some reflexion at edge when overbloomed.
- *Fragrance.*—Chrysanthemum.

Reproductive organs:

- *Stamen.*—Normal for single.
- *Pollen.*—A few appear when blooming.
- *Styles.*—Green yellow; columnar, 8 mm. long (approx.).
- *Length.*—Medium.
- *Stigmas.*—Normal Yellow with a width of 1 mm. (approx.).
- *Ovaries.*—Enclosed in calyx.

Plant:

- *Form.*—Herbaceous.
- *Growth.*—Vigorous.
- *Height.*—Tall, 100 cm. (approx.).

*Peduncle.*—Strong. Near the top — 15 cm. Near the middle — 24 cm. Near the bottom — 27 cm.

*Internodes.*—2.5–4 cm.

*Response time.*—8.5 to 9 weeks.

Foliage:

*Color.*—Normal green.

*Size.*—Medium, length 12.5 cm. and width 7.5 cm. (approx.).

*Quantity.*—Normal to less.

*Shape.*—Pointed.

*Texture.*—Upper and underside smooth.

*Ribs and veins.*—Normal.

*Margin.*—Deep undulated.

*Leaf (upper and underside).*—Very rough.

In the description above, color references are made to the "Horticultural Colour Chart I & II" issued by The British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinctive variety of Chrysanthemum named 'White Refla', as described and illustrated in the foregoing specification and accompanying drawings.

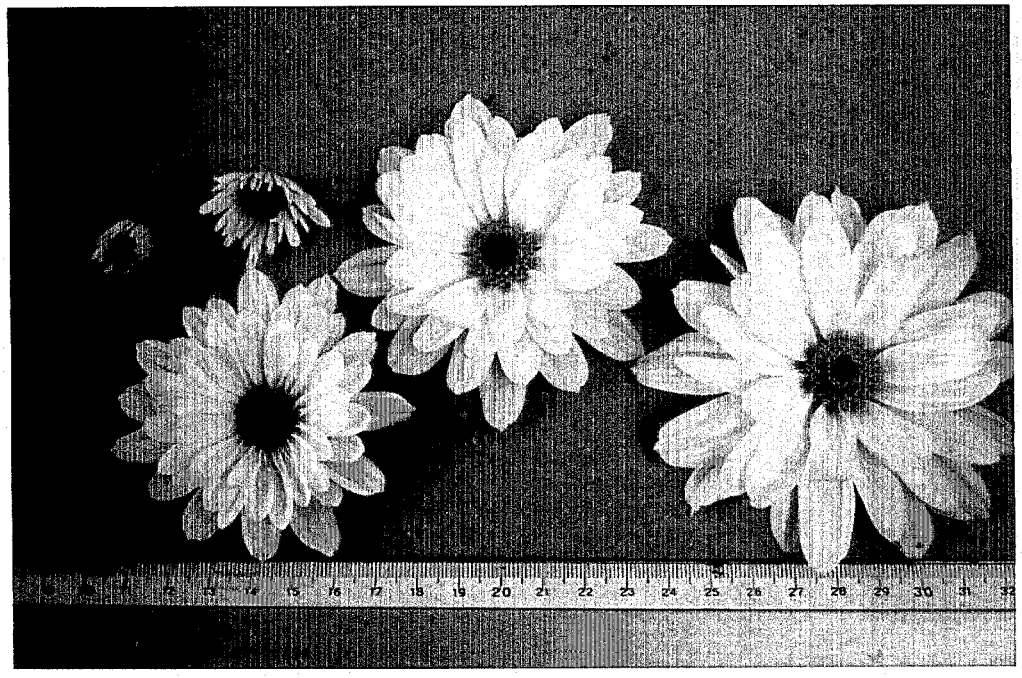

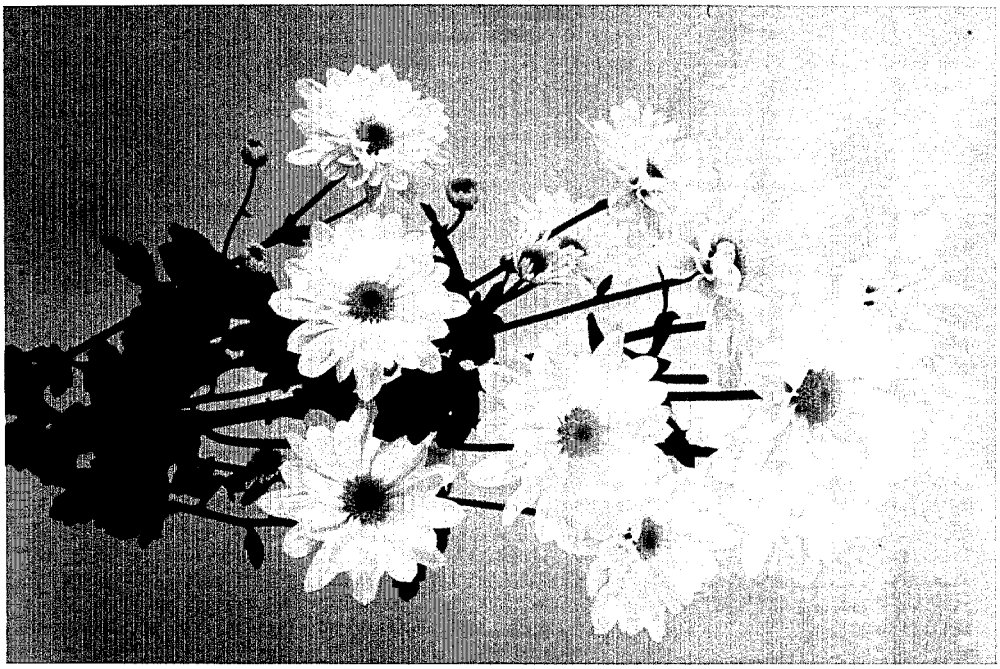
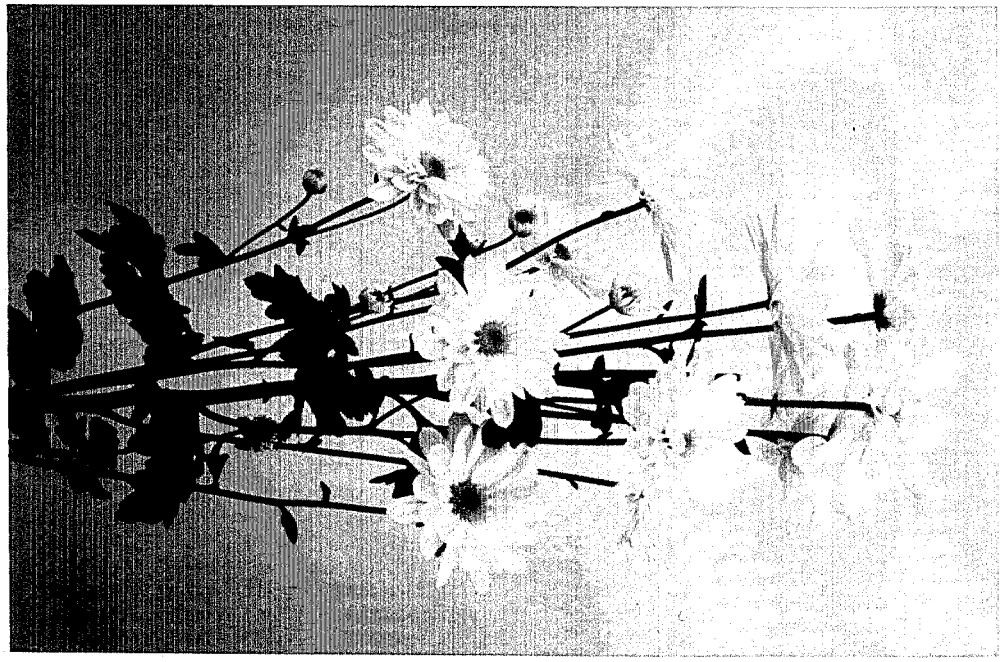

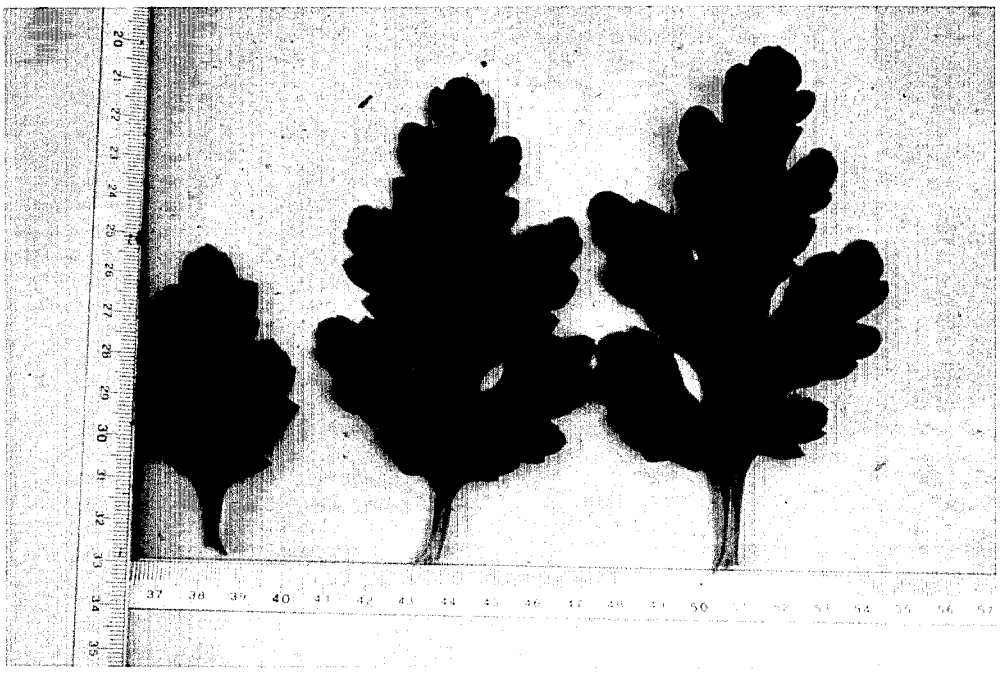
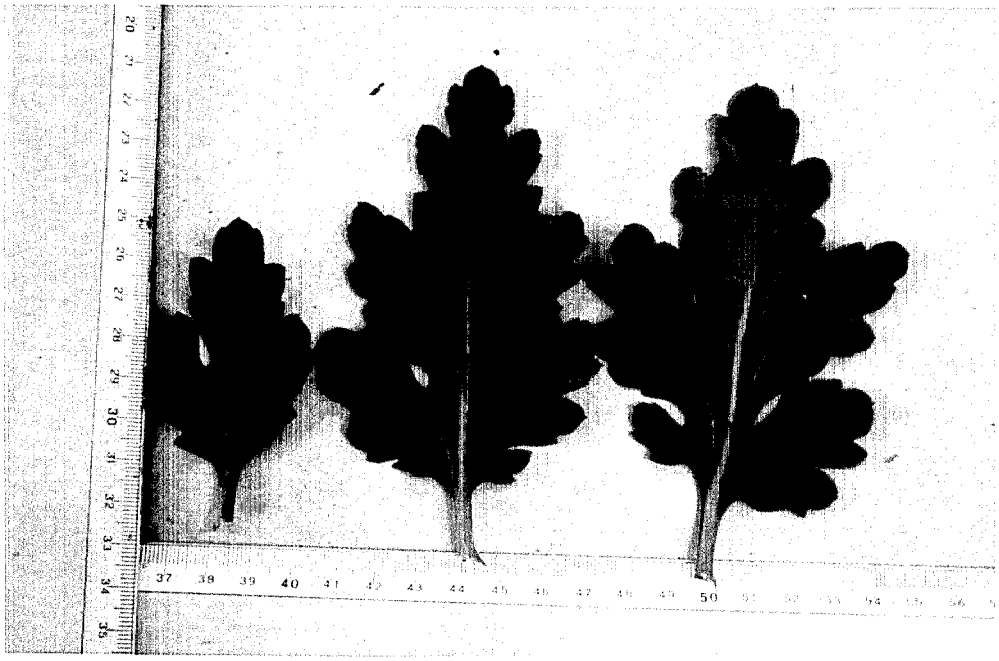

* * * * *